United States Patent [19]

White et al.

[11] Patent Number: 4,739,755
[45] Date of Patent: Apr. 26, 1988

[54] RESPIRATOR

[75] Inventors: Willard C. White, Huntington; Kevin D. Rodgers, Sr., Medford; Jay A. Parker, Flushing, all of N.Y.

[73] Assignee: American Cyanamid Company, Stamford, Conn.

[21] Appl. No.: 920,570

[22] Filed: Oct. 17, 1986

[51] Int. Cl.⁴ ............................................. A62B 7/00
[52] U.S. Cl. ........................... 128/206.12; 128/206.21; 128/206.24
[58] Field of Search ...................... 128/206.12, 206.15, 128/206.21, 206.24, 206.17

[56] References Cited

U.S. PATENT DOCUMENTS 2,382,364  8/1945  Tant ................................. 128/206.24
2,505,173  4/1950  Conley .............................. 128/206.17

FOREIGN PATENT DOCUMENTS 1282992 12/1961  France ............................. 128/206.24
 321483 10/1934  Italy ................................ 128/206.24
1191793  5/1970  United Kingdom ........... 128/206.24

Primary Examiner—Edward M. Coven
Assistant Examiner—J. P. Lacyk
Attorney, Agent, or Firm—Gordon L. Hart

[57] ABSTRACT

The device relates to a mask worn over a wearer's face for air filtration. The mask has an inturned lip that forms a seal on the edge of the mask with the wearer's face. The mask also has at least two other contact surfaces, internal to the edge seal, which vary in length to increase the seal integrity of the mask. The mask has an exhalation valve in the front in direct line of expelled breath and a plurality of horizontal pleats below the exhalation valve such that the wearer can talk without substantial movement of the sealing edge. The mask also has two inhalation valves on each side, over the cheeks, to allow air to enter the mask.

9 Claims, 2 Drawing Sheets

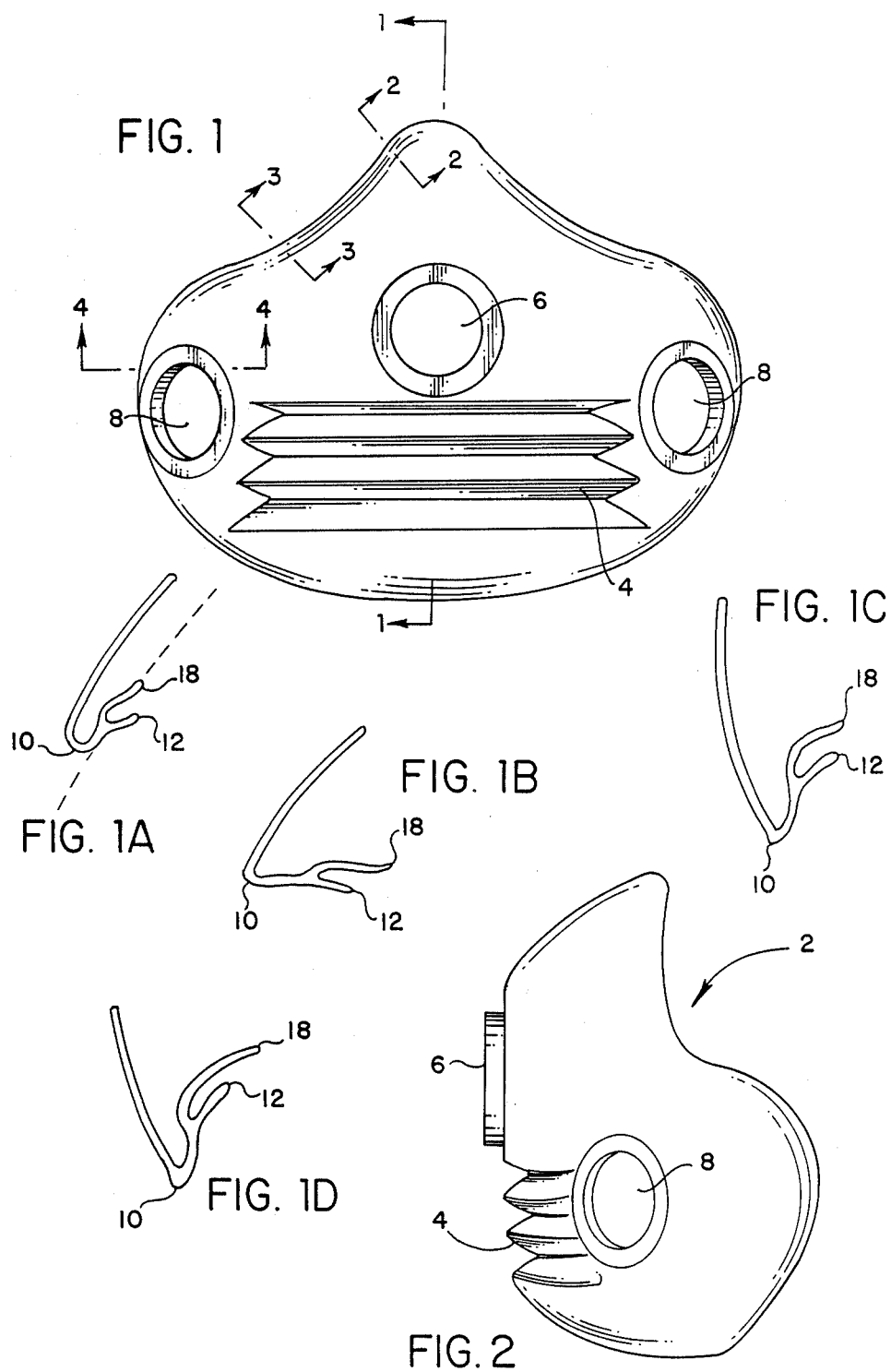

RESPIRATOR

FIELD OF THE INVENTION

The present invention relates to the air filtration or purification art, more specifically to a device worn over the face for air filtration, and specifically to an air filtering device which increases wearer comfort while increasing respirator performance.

BACKGROUND OF THE INVENTION

Work is continuously being done to provide maximum protection in the area of air filtering while minimizing discomfort to the wearer of a mask designed for air filtering and purification.

The type of respirator to which the present invention is related is the respirator which utilizes a half-mask or full face mask which covers the nose and mouth and/or the entire face.

In attempting to increase protection afforded through the use of a mask-type respirator a two-point seal has previously been disclosed. Matheson, et al., U.S. Pat. No. 4,414,973, teaches the use of a stiffening outer flange, or lip seal comprising a blunt edge and internal to that a curved seal to more easily conform to a wearer's face. Likewise, Lehmberg, U.S. Pat. No. 2,166,164, teaches the use of an internal and external seal but only in the cheek area. The Lehmberg respirator double seal is very similar to Matheson, et al. in that it comprised a blunt outer and a curved inner seal.

The present invention increases the integrity of the seal through the employment of multiple flexible contact surfaces between the mask and the face. Two or more contact surfaces are used, the one most external being a flexible inturned lip and the remaining one or more being flexible and feathered inward toward the face creating multiple pressure pockets.

The further addition of horizontal pleats in a horizontally elongated frontal portion of the mask allows greater jaw and mouth movement for ease of talking with less shifting of the seal, thereby maximizing protection by the mask against the intrusion of unfiltered air. Although Fink, U.S. Pat. No. 2,376,871, teaches the use of corrugations or ribs to permit jaw movement, these extend from the jaw hinge points on one side of the face to the other. The present invention uses pleats only on the front of the mask with a wrap around design of the mask, covering the jaw area. Location of these pleats provide a comfortable fit to wearers of varied sizes.

Increased comfort is also provided by use of this invention through the location of the inhalation and exhalation ports on the mask releasing expelled air directly and allowing fresh air to enter laterally and bathe over the face, keeping the enclosed portions of the wearer's face cool.

It is a primary object of the present invention to provide an orinasal respirator with an improved seal to exclude air from passing between portions of the mask and the face of the wearer even during movement, thereby lowering physical restrictions generally created by use of a respirator.

It is a further object of the present invention to provide for vertical expansion and contraction of the mask during movement of the mouth to decrease seal shifting thereby creating a seal with added integrity.

It is another object of the present invention to increase wearer comfort by facilitating the immediate release of hot, moist expelled gases through the location of an exhalation port or ports in the direct line of expelled breath and locating the inhalation ports on the outer sides of the mask so as to allow fresh, cool air to circulate over the wearer's face.

SUMMARY OF THE INVENTION

The foregoing objects and other objects inherent from the following disclosure are accomplished by the present invention and method for use thereof.

The invention in its broadest aspect comprises a device for filtering or purifying air to be worn over the face, and especially over the mouth and nose, which maintains a secure seal of the mask to the face even during movement and talking, while increasing wearer comfort.

The increased seal integrity of the respirator described herein is maintained through the use of multiple contact points, or intermediate seals, which create independent pressure pockets or areas between the seals. These intermediate contact surfaces are flexible to maintain contour to the face even during slight shifting, and pointed inward on the face to increase contact ability during movement of the mask, thereby further limiting intrusion of air into the mask. Individual pressure pockets demonstrate the increased integrity of the seal between the atmosphere and interior of the mask where the additional contact surfaces act as multiple, individual barriers to the atmosphere. Even if there is shifting during movement, seal integrity is maintained by the flexibility of the intermediate seals working to keep in contact with the face and multiple contact surfaces as additional lines of defense against the atmosphere. These improvements lower physical restrictions on the wearer during use of the respirator.

Means are included for allowing vertical expansion and contraction of the mask in the front lower portion of the mask combined with a horizontally elongated mask structure for maintaining the integrity of the seal and providing wearer comfort during movement of the jaw and mouth during talking. This means permits the wearer to talk more freely by allowing vertical mouth movement under the mask without substantial shifting of the mask on the face, shifting causing the likelihood of air entering between the mask and the face. Also, a wider range of face sizes can be fitted by the use of these means.

The mask described herein further increases wearer comfort through the location of the inhalation and exhalation ports. One or more one-way exhalation valve ports are located in a direct line with expelled air, i.e., directly in front of the mouth and nose. This placement allows expelled air to exit the mask easily and not be withheld in the interior of the mask. This is important because expelled air is hot and contains moisture which will make the wearer's skin under the mask uncomfortable during periods of extended wear. Wearer comfort is further enhanced by lateral placement of one or more inhalation ports to the outside of the mask over the check area. Lateral placement of the inhalation ports allows the fresh air to be taken in over the face, thereby keeping the skin under the mask cool and comfortable.

BRIEF DESCRIPTION OF THE DRAWINGS

FIG. 1 is a front elevational view of a respirator mask in accordance with the invention.

FIG. 1A is a cross-sectional view of the mask edge through line 2—2 of FIG. 1.

FIG. 1B is a cross-sectional view of the mask edge through line 3—3 of FIG. 1.

FIG. 1C is a cross-sectional view of the mask edge through line 4—4 of FIG. 1.

FIG. 1D is a detail of the mask edge of the lower portion of a cross-section through line 1—1.

FIG. 2 is a side elevational view of the respirator.

FIG. 3 is a back elevational view of the respirator.

DESCRIPTION OF THE PREFERRED EMBODIMENT

Figure 5:
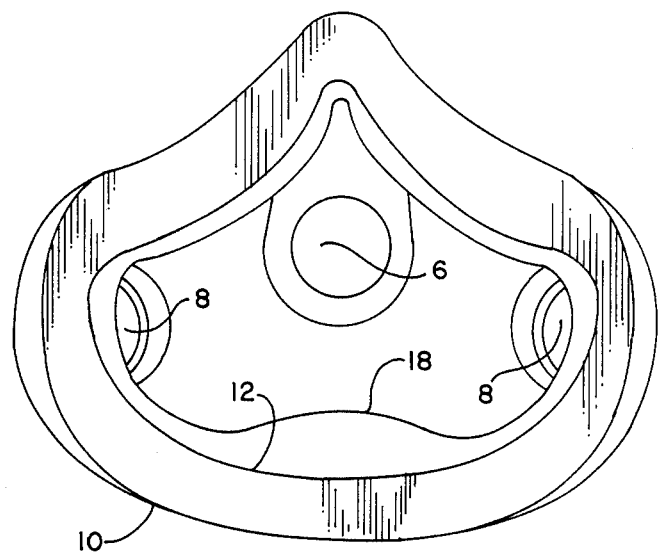
Figure 4:
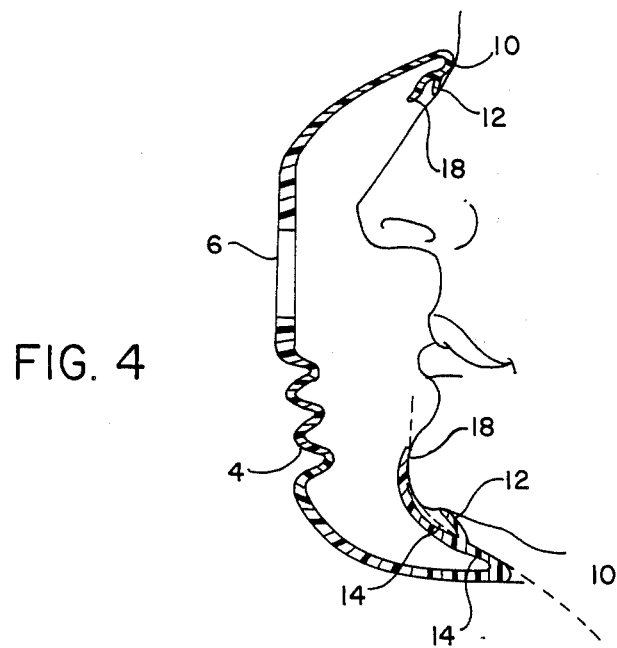
FIG. 4 is a cross-section of the mask through line 1—1 of FIG. 1, also showing conformation of the mask to the face of a wearer.

Referring to the drawings, reference numeral 2 designates, in general, a respirator mask contructed in accordance with the teachings of the present invention. The mask 2 is formed substantially in the shape of the portion of the face which it covers from a mostly flexible material, silicone rubber being most preferred, to allow contour to the face of the wearer for an effective seal. In the preferred embodiment, a half mask is employed, covering the nose and mouth of the worker, starting at the bridge of the nose, running across the cheeks and along the bottom of the chin, forming an airtight seal.

As seen in FIGS. 1A-1D and, the mask edge 10 comprises form fitting portions which help provide an air tight seal further comprising additional interior projections, or intermediate seals 12, and an inner seal 18 pointing inward along the face. The mask edge 10 is of the turnover type, having an inturned lip as the outer contact surface of the mask 2 to the wearer's face. This turnover edge 10 extends on the face and ends providing another contact point, most internal within the mask 2, known as the primary inner seal 18. The intermediate seal or seals 12 are located between the mask edge 10 and the primary inner seal 18. The number of intermediate contact surfaces 12 can be varied, the preferred embodiment containing one (1) intermediate seal 12 between the mask edge 10 and the inner contact surface 18 (see FIGS. 1A-1D). The intermediate seal 12 are feathered and flexible to allow them to maintain their position on the face even when the respirator 2 shifts slightly. The mask 2 makes contact with the wearer's face at the mask edge 10, at each of the intermediate seals 12, and creating individual pressure pockets 14 between the primary inner seal 18 at the contact points. Flexibility of the intermediate seals 12 provide contact surfaces which hold the face contour even during shifting. To accomplish this the length of the extension comprising the intermediate seal 12 varies along the perimeter of the mask 2, being the shortest at the bridge of the nose and the longest in the chin area. The pressure pockets 14, created between the contact surfaces and the face, provide increased seal integrity with additional barriers between the environment and the internal mask area. These additional flexible barriers 12 maintain a superior seal thereby lowering physical restrictions and allowing freer movement by the wearer without leakage of air into the mask 2 from the mask edge 10 at face contact points.

Pleats 4 on an elongated mask front are the preferred structure for providing a means to allow vertical expansion and contraction of a portion of the mask 2 relating to jaw movement and movement of the mouth for talking (see FIGS. 1 and 2). In the preferred embodiment the pleats 4 comprises an area 4 inches wide and 1¾ inches high on the front of the mask 2. The number of pleats 4 is not of great importance as long as they are sufficient in number and size to allow accordion type vertical expansion and and contraction of between ¾ and 1¾ inches. The bigger the pleats 4 the fewer will be necessary to provide said vertical lift, likewise, a greater number of smaller pleats 4 will be necessary to achieve the same vertical lift.

For example, three (3) pleats 4 comprising five (5) folds of ½ inch between folds provides the desired vertical lift for normal use. Elongation of the mask width further provides freer jaw movement and the combination of pleats 4 and elongation provide a better fit for a greater variety of facial sizes.

A key feature of the preferred embodiment is to provide width sufficient to wrap around the user's face extending almost to the sideburn area. In contrast to the prior art, this provides for the greatest freedom of jaw movement without risk of breaking the seal, and it permits use with lower headband tension and allows for longer periods of comfortable wear. Prior art devices which do not have sufficient wrap around rest on the cheekbones, and distort the skin and can be exceedingly uncomfortable after relatively short periods of wear.

In general, the ratio of the maximum distance measured horizontally from edge to edge to the maximum distance measured vertically from edge to edge will be in excess of 1.0:1 and preferably in excess of 1.5 to 1 and most preferably in excess of about 2.0 to 1. In any event, the ratio should not exceed 3.0 to 1, which puts the edges into the sideburns and also can fail to adequately cover the entire nose and chin. Usually, the prior art employs ratios of less than 1.0 to 1 which has the drawback of lack of comfort.

Provision of a seal having multiple, flexible intermediate contact points 12 which more readily retain their original placement on the face, including a structural means for allowing vertical expansion during mouth movement and a wrap around design extending the mask 2 farther back on the sides of the face maximizes worker protection from unfiltered air thereby increasing user comfort.

The wearer's comfort is further increased through use of the present invention due to placement of the exhalation 6 and inhalation 8 ports (see FIGS. 1, 2 and 3). A one-way exhaust port 6 is placed on the front, middle portion of the mask 2 in a direct line with the expelled breath of the wearer. Since expelled breath is hot, moist air, it is uncomfortable for the wearer to allow it to build up inside the mask 2. The one-way exhalation port 6 placed in the direct line of expelled breath allows easy exit of the hot, moist air without substantial retention within the mask 2. Lateral placement of the inhalation ports 8 toward the outside portions of the mask 2 is provided to allow cool, fresh air to be drawn in over the portion of the face enclosed by the mask 2 thereby bathing the enclosed face in the cool, fresh air and increasing comfort of the wearer by limiting build-up of stagnant, hot and humid air.

The inhalation ports 8 comprise cannister filtering devices such as chemical cartridges, high efficiency filters, or other known in the art located 2¾ inches from the side ends of the mask and are attached to the inhalation valves. The inhalation valves are in only check valves of the flapper variety being approximately 1⅜ inches in diameter. The inhalation valves can also be attached to a self-contained air supply if filtering is sufficient in the designated atmospheric conditions.

In preferred embodiments, the exhalation valve is an out only check valve of the mushroom flapper type being approximately 1½ inches in diameter.

The mask 2 is maintained firmly on the wearer's face by a suitable device known in the art designed to maintain a constant pressure of the mask 2 on the wearer's face. The preferred maitenance device comprises a yoke which fits over the front of the mask 2, with openings over the inhalation and exhalation valve areas, which does not interfere with the vertical expansion and contraction feature of the pleats 4, also on the front of the mask 2. The yoke has attachment points on the corners to attach head bands adapted to conform to the wearers head.

We claim:

1. A respirator mask for filtering or purifying air adapted to be worn over the face which comprises
   (i) an inturned lip forming a turnover seal edge as the outer contact surface for sealing contact of the edge of the mask to the wearer's face and means for increasing seal integrity comprising at least two other contact surfaces each comprising a feathered flexible extension of the inturned lip internal to the turnover seal edge, each extension angled inwardly to the face and making acontact with the face, the most interior of which is a primary inner seal at the inner edge of the inturned lip, and at least one other such extension extending from the inturned lip between the primary inner seal and the turnover edge seal, each of said flexible extensions varying in length around the mask, being shorter at the nose and longer at the chin, whereby each of said contact surfaces makes sealing contact with the face along the perimeter of the mask providing multiple pressure pockets between the multiple seals and less chance for leaks, and
   (ii) a plurality of horizontal pleats across the front lower portion of the mask for vertical expansion and contraction to facilitate talking by the wearer without substantial movement of the turnover seal edge, and
   (iii) one or more one-way exhalation valves at the front of the mask above said pleats and in the direct line of expelled breath to allow expelled breath to exit the mask through said valves and
   (iv) two or more one-way inhalation valves, one on each side of said mask over the cheeks to allow air to enter the mask and flow across the face.

2. A mask as in claim 1 wherein the horizontal pleating is about 4 inches wide and about 1⅜ inches high on the front lower portions of said mask allowing vertical expansion and contraction of between ¾ and 1¾ inches.

3. A mask as in claim 2 wherein the exhalation valve is an out only check valve of the flapper type being 1.45+0.1 inches in diameter.

4. A mask as in claim 3 wherein the inhalation valves are in only check valves of the flapper type capable of attachment to cannister filters located 2¾ inches from the side ends of the mask and are 1.35+0.1 inches in diameter.

5. A mask as in claim 4 comprising one intermediate contact surface between the outer contact surface and the primary inner contact surface.

6. A mask as defined in claim 1 wherein the ratio of the maximum length measured horizontally from edge to edge to the maximum length measured vertically edge to edge is greater than about 1.0:1.

7. A mask as in claim 6 wherein the ratio of the maximum length measured horizontally from edge to edge to the maximum length measured vertically from edge to edge is in excess of about 2.0:1.

8. A mask as in claim 7 formed from materials characteristically similar to materials from the group consisting essentially of silicone rubber, natural rubber, polyvinyl chloride, and neoprene rubber.

9. A mask as in claim 8 formed from silicone rubber.

* * * * *